United States Patent
Monginoux et al.

(10) Patent No.: US 10,548,867 B2
(45) Date of Patent: Feb. 4, 2020

(54) SOOTHING COMPOSITION FOR ANIMALS, COMPRISING AT LEAST ONE FATTY ACID AND NEPETALACTONE

(71) Applicant: VIRBAC, Carros (FR)

(72) Inventors: Patricia Monginoux, Villeneuve Loubet (FR); Olivier Guerret, Pern (FR); Samuel Dufour, Orthez (FR)

(73) Assignee: VIRBAC, Carros (FR)

( * ) Notice: Subject to any disclaimer, the term of this patent is extended or adjusted under 35 U.S.C. 154(b) by 0 days.

(21) Appl. No.: 15/537,994

(22) PCT Filed: Dec. 18, 2015

(86) PCT No.: PCT/IB2015/059793
§ 371 (c)(1),
(2) Date: Jun. 20, 2017

(87) PCT Pub. No.: WO2016/103133
PCT Pub. Date: Jun. 30, 2016

(65) Prior Publication Data
US 2017/0348267 A1     Dec. 7, 2017

(30) Foreign Application Priority Data
Dec. 24, 2014    (FR) ..................................... 14 63323

(51) Int. Cl.
*A61K 31/20* (2006.01)
*A61K 9/08* (2006.01)
*A61K 9/00* (2006.01)
*A61K 31/365* (2006.01)

(52) U.S. Cl.
CPC .............. *A61K 31/20* (2013.01); *A61K 9/007* (2013.01); *A61K 9/08* (2013.01); *A61K 31/365* (2013.01)

(58) Field of Classification Search
CPC .......... A61K 31/20; A61K 47/10; A61K 9/08; A61K 31/201; A61K 31/202; A61K 31/366; A61K 36/53; A61K 9/005; A61K 31/365
See application file for complete search history.

(56) References Cited

U.S. PATENT DOCUMENTS

| | | | | |
|---|---|---|---|---|
| 6,384,252 | B1 * | 5/2002 | Pageat | A61K 31/20 554/223 |
| 2011/0150822 | A1 | 6/2011 | Nouvel et al. | |
| 2013/0261193 | A1 * | 10/2013 | Nouvel | A61K 9/007 514/762 |
| 2013/0340686 | A1 * | 12/2013 | Pageat | A01N 37/02 119/712 |

FOREIGN PATENT DOCUMENTS

| | | |
|---|---|---|
| AU | 2007-100-281 A4 | 9/2007 |
| EP | 0724832 A1 | 8/1996 |
| EP | 1066829 A1 | 1/2001 |
| GB | 2345635 A | 7/2000 |

OTHER PUBLICATIONS

Modnicki et al. Acta Poloniae Pharmaceutica ñ Drug Research, vol. 64 No. 3 pp. 247ñ252, 2007.*
Dow (1992) 6 pages.*
International Search Report issued in corresponding International Patent Application No. PCT/IB2015/059793 dated Mar. 4, 2016.
Chezpara.fr, "Feliway Solution a Vaporiser 60ml," (2014).
Pageat et al., "Current research in canine and feline pheromones," Veterinary Clinics of North America, 33: 187-211 (2003).
Tucker et al., "Catnip and the catnip response," Economic Botany, 42: 214-231 (1988).

* cited by examiner

*Primary Examiner* — Shirley V Gembeh
(74) *Attorney, Agent, or Firm* — Christensen O'Connor Johnson Kindness PLLC

(57) ABSTRACT

The invention relates to novel soothing compositions for animals, particularly for cats. It specifically relates to soothing compositions for non-human mammals, comprising between 1% and 50% w/w of at least one fatty acid comprising between 5 and 22 carbon atoms and between 0.01% and 5% w/w of nepetalactone, such that said at least one fatty acid and said nepetalactone are dissolved in a solvent. Said compositions are characterised in that they exhibit soothing properties for stressed animals and are stable for the entire period of use thereof.

12 Claims, 1 Drawing Sheet

SOOTHING COMPOSITION FOR ANIMALS, COMPRISING AT LEAST ONE FATTY ACID AND NEPETALACTONE

The present invention relates to novel soothing compositions for animals, in particular cats; it more particularly targets compositions combining fatty acids which constitute synthetic cat facial pheromones with nepetalactone. These compositions have the particular feature of having soothing properties for the animal in the event of stress, and are stable over the duration of their use.

The problem of soothing animals, whether they are pets or livestock, is a significant problem which has been widely studied in the prior art. Indeed, the products used are of significant economic importance and owners have a need to combat unpleasant behavior and symptoms in domesticated animals, in particular dogs and/or cats, and for livestock farmers there is an economic importance in soothing the livestock in order to increase their productivity.

For example, felines in general, and cats in particular, exhibit very specific and instinctive symptoms of stress or anxiety, such as clawing or scratching or else urine marking. The latter consists of urinating in various areas of a room, with the aim, especially, of marking their territory and thereby of creating a more reassuring space for the animal. By these actions, cats deposit odoriferous molecules which they can identify. However, it is obvious that these different behaviors represent significant problems in terms of health and cleanliness which may inconvenience cat owners.

Various studies have made it possible to identify the molecules that cats use to mark their territory, in order to develop compositions which make it possible to soothe them, and to limit behavior which is inconvenient to humans.

Thus, the first studies by P. Pageat demonstrated that cats have facial pheromones, including the F3 fraction, which act in a soothing way on the cat. The development of a formula containing a synthetic replica of this F3 fraction in a mixture of pimelic acid, azelaic acid, palmitic acid and oleic acid was subsequently described in the document EP0724832. In this document, the F3 fraction is combined with valerian extracts in emulsion mixtures. Since the valerian has an attractant character for cats, it attracts the cat towards the area of diffusion, where the F3 fraction performs its soothing role.

Studies on the method of diffusion of the compositions based on the synthetic replica of the F3 fraction were then carried out, in order to solve the problems inherent to these molecules and to their method of application. These problems are varied: chemical stability (esterification or oxidation of the fatty acids), physical stability (crystallization), rate of diffusion (due to the high viscosity of the pure F3 fraction).

Thus, in the document EP1066829, the authors explain that compositions comprising fatty acids such as those in the F3 fraction are very viscous and require solubilization in an alcohol. Since the chemical stability of the fatty acids in the presence of alcohol is problematic, the authors chose to formulate the F3 fraction in micro-emulsions using surfactants of stearate type.

Another approach, described in the document WO2009144321, consisted in depositing the F3 fraction on cellulose supports which are then used in electric diffusers to thermally regulate an F3 fraction release profile.

Apart from these pioneering studies, other semiochemical substances have been discovered. For example, in the document WO9937297, the authors report that substances originating from the mammary glands of mammals also have a soothing effect. Once again, the chemical compositions identified are mixtures of fatty acids, especially mixtures of linoleic, oleic and palmitic acids. The studies illustrated in the documents US20110150822 and US20130210927 are other examples of this type of composition, in which, in this case, mixtures of fatty acids and of squalene or else an interomone, are disclosed.

These compositions nonetheless have the same problems of formulation and of controlled release over the entire duration of exposure to the soothing treatment. Moreover, olfactory communication in cats cannot be reduced to pheromones alone, since conventional odors also influence feline behavior. Nonetheless, since attention has been drawn to pheromone communication, conventional olfactory communication has been set aside by the veterinary sciences.

Nepetalactone is a soothing attractant known to those skilled in the art. The response to nepetalactone is restricted to olfactory stimulation only in cats, without however involving the vomeronasal organ (Hart and Leedy 1985). Moreover, this response is independent of the state of the gonads and is clearly associated with pleasure behavior in cats (Hatch 1972, Hart 1974).

The odor of nepetalactone is highly attractive to different felines (whether wild cats or domestic cats) in a dosage-dependent manner, even at low doses in domestic cats (0.01-0.1 mg), and interest decreases at doses of around 0.001 mg. It is known that exposure to nepetalactone improves the general well-being of cats, facilitates happy behavior and social interactions, and induces soothing effects. In addition, nepetalactone is a known attractant. This molecule is the active agent which explains the attractiveness of herbaceous plants of the *Nepeta* family. Nepetalactone is a terpenoid having 3 asymmetrical centers, the ratio of the different isomers varying depending on the *Nepeta* varieties it originates from. The nomenclature of these isomers is defined by numbering atoms of nepetalactone:

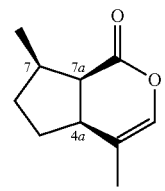

There are eight stereoisomers of nepetalactone, but the products originating from nature have an S configuration at carbon 7. These are therefore the isomers 4aβ,7α,7aβ; 4aβ,7α,7aβ; 4aα,7α,7aα; 4aα,7α,7aβ (also referred to, respectively, as cis,cis; trans,trans; cis,trans; trans,cis). In the paper by F. Senatore et al. (Chemistry & Biodiversity, vol 8, 2011, p. 1987), there is a complete review of the natural sources of nepetalactone (and thus of the different isomers present in each *Nepeta* species).

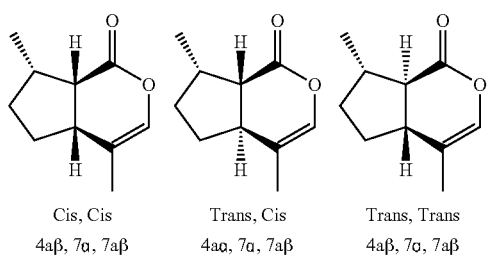

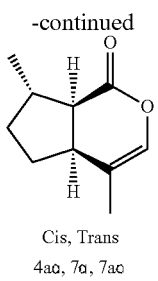

Cis, Trans
4aα, 7α, 7aα

*Nepeta cataria*, known as common catnip, has the highest concentration of nepetalactone. Depending on its origin, it may contain the 4 isomers 4aα,7α,7aα; 4aβ,7α,7aβ; 4aα, 7α,7aβ; 4aβ,7α,7aα, but also the isomer 4aα,7β,7aα. The abundance of the isomers in catnip may depend on the region in which it grows, but it appears that all the isomers of nepetalactone have an attractant effect on cats.

Industrially, nepetalactone may be obtained either synthetically, or by extraction from catnip, as summarized in the review by Birkett et al. (Phytochemistry 62 (2003) 651-656).

A homogenous composition of nepetalactone combined with fatty acids, preferably with the synthetic analog of the F3 fraction, and enabling homogenous release by diffusion represents an ideal solution for preventing and soothing stress in cats and for causing the symptoms associated therewith to disappear in a highly effective manner.

Indeed, not only will nepetalactone, due to its attractant nature for cats, make it possible to attract cats into the area where the composition has been diffused, but also fatty acids, preferably the synthetic analog of the F3 fraction, will make it possible to prevent the stress felt by cats and to soothe cats, which will make it possible, inter alia, to avoid future marking, such as urine marking and scratching. In addition, as has been discovered in the present invention, nepetalactone, in the purified form of natural origin or synthetic origin, or else in the form of plant extracts, in particular from the *Nepeta* family, makes it possible to significantly reinforce the soothing effect of the fatty acids and contributes to soothing stress in cats, to cause the symptoms associated therewith to disappear more effectively.

The difficulty in developing such compositions arises from the fact that nepetalactone belongs to the chemical family of the lactones. The following scheme explains the reactivity of these molecules:

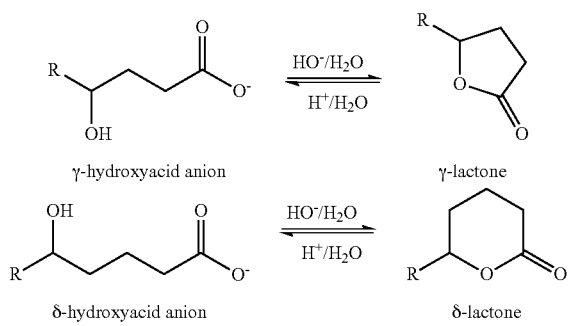

γ-hydroxyacid anion     γ-lactone

δ-hydroxyacid anion     δ-lactone

Lactones are formed in basic medium and are hydrolyzed in acidic medium. This is also the case for the lactones of the nepetalactone family (see A. Bianco, Pure & Appl. Chem., Vol. 66, 1011 1, pp. 2335-2338, 1994). In the presence of carboxylic acid, transesterifications may still occur. One way to avoid these transesterifications could consist in using basic acid salts rather than the acidic form thereof. However, acid salts cannot be used for a soothing pheromone without posing problems of distribution of the product because they do not evaporate. Indeed, in order for nepetalactone to effectively play the role of attracting the animal, it is necessary for it to diffuse into the atmosphere, in order to be smelt and detected by the animal over the necessary duration of exposure to the soothing composition. Thus, the compositions according to the invention are solutions which enable satisfactory evaporation of the various constituents of the composition, both the fatty acids and the nepetalactone.

Moreover, the duration of exposure or of treatment of cats, in order to habituate them to a new environment, is of the order of a month, which is a very long duration within the context of the chemical reactions between the various constituents of a complex composition. It therefore proves very difficult to combine nepetalactone with a synthetic replica of the F3 fraction of the cat facial pheromone, or even with one or more fatty acids in a homogeneous liquid composition, the constituents of which cannot be distinguished with the naked eye after stirring, and which is effective over the required duration without any major chemical conversions taking place over the duration of the treatment. Such conversions serve to denature the constituents and particularly nepetalactone, which then becomes unavailable. The physical and chemical stability of nepetalactone within the soothing composition must therefore be satisfactorily ensured.

In application GB2345635 the authors attempted to solve the problem by encapsulating a combination comprising especially nepetalactone and fatty acids. However, such a composition is not easy to employ since encapsulation is a complex and expensive process. Moreover, encapsulation prevents the diffusion of the fatty acids, which limits the mode of action of the soothing system to a contact mode, the friction of the cat on the capsules being in this case necessary in order to release the fatty acids.

Document AU2007100281 describes a calming composition for animals, capable of reducing the emission of unpleasant odors resulting from microbial activity of microorganisms present on the animal, of absorbing any unpleasant odors from the animal and of fragrancing it; this is a complex aqueous composition combining animal pheromones with an attractant substance such as an extract of *Nepeta cataria* and comprising in particular non-complexed cyclodextrins capable of capturing malodorous substances, antibacterial agents including chlorhexidine and antimicrobial agents in order to eliminate the microorganisms, and fragrance. The stability of this composition, and in particular that of the extract of *Nepeta cataria*, is not, however, described; nor is its duration of action. In addition, the proportion of different ingredients contained in this composition is very different to that of the compositions according to the invention.

To the applicant's knowledge, there is not currently any homogeneous liquid composition of nepetalactone and fatty acid which enables release by diffusion; the applicant therefore set itself the aim of remedying this lack.

The inventors have thus developed compositions, uses and methods which especially make it possible to reduce repetitive urine marking which occurs in the case of stress and/or a state of anxiety in non-human mammals, linked, for example, to particular circumstances or changes in their immediate environment. The compositions, uses and methods according to the invention also make it possible to improve the conditions for familiarization of non-human mammals with their new environment and/or to prevent, for example, clawing and scratching or the destruction of the territory and/or to reduce auditory manifestations (such as meowing, whining and growling). The beneficial effects can be measured by the reduction in urine marking and scratching and by the repetition of physical contact or rubbing against new objects or individuals which surround them. More generally, due to their content of fatty acids, the compositions according to the invention make it possible to improve the general behavior of non-human mammals with regard to their environment and the people present in this environment, especially with a reduction in stress, anxiety, urine marking and/or auditory manifestations, and also with behavior which is less aggressive, more relaxed and more affectionate especially with their owners.

The inventors have also found, surprisingly, that by suitably adjusting the concentrations of fatty acid (and in particular of the F3 fraction) and of nepetalactone, it was possible to diffuse mixtures of nepetalactone and of fatty acid, in particular of synthetic F3 fraction of the cat facial pheromone, for longer periods than required for exposure and treatment of the cat.

The present invention thus relates to a soothing composition for non-human mammals, comprising between 1% and 50% by weight/weight of at least one fatty acid comprising between 5 and 22 carbon atoms and between 0.01% and 5% by weight/weight of nepetalactone, characterized in that said fatty acid(s) and said nepetalactone are dissolved in a solvent.

The non-human mammal is more particularly a feline and even more particularly a cat, especially a domestic cat.

The composition according to the invention is particularly effective on cats in a broad sense, including all the members of the Felidae family or felines, including domestic cats, and more generally all breeds of cats, and also tigers, lions, leopards, mountain lions, lynxes, bobcats, ocelots and the like.

According to the invention, fatty acid is intended to mean monocarboxylic acids with a saturated or unsaturated, linear or branched hydrocarbon-based chain. More specifically, these fatty acids are chemical substances liable to alter the behavior or the physiological responses of the animal.

The content of fatty acid in the composition is preferably between 1% and 20% by weight/weight and even more preferentially between 1% and 15% by weight/weight.

The fatty acids used, alone or in a mixture, preferably contain between 5 and 22 carbon atoms; nonlimiting examples thereof are capric, lauric, azelaic, myristic, palmitic, palmitoleic, oleic, linoleic, linolenic, stearic, arachidonic, caproic, pivalic, gamma-linoleic, pimelic, eicosapentanoic, docosahexanoic, pentadecanoic and tridecanoic acids.

The composition according to the invention preferably comprises a fatty acid chosen from oleic, linoleic, linolenic, palmitic, myristic, azelaic, pimelic, capric or lauric acid, or else a mixture of a least two fatty acids from the preceding list. Even more preferentially, the composition according to the invention comprises at least one fatty acid chosen from oleic, pimelic, azelaic and palmitic acid.

The compositions according to the invention may contain any derivatives of fatty acids, such as, for example, esters of fatty acids.

The derivatives of fatty acids used, alone or in a mixture, are preferably derivatives of fatty acids consisting of 5 to 22 carbon atoms. Nonlimiting examples thereof are ethyl pimelate, diethyl pimelate, monomethyl nonanedioate, ethyl decanoate, ethyl laurate, ethyl palmitate and ethyl oleate.

According to a particular embodiment of the invention, the composition comprises a mixture of fatty acids corresponding to the fatty acids which constitute the F3 fraction of the cat facial pheromones; the composition of fatty acids of this fraction is known to those skilled in the art, since it has been widely described in the prior art; this mixture may for example be replicated synthetically as described in example 3 below.

According to the invention, pheromones is intended to mean a substance released by the body of certain species, which substance acts as messengers between individuals, said substance being able to serve especially to communicate, or else as a specific attractant, for example in sexual attraction.

Another of the features of the composition according to the invention is such that the ingredients that it comprises are in solution.

Solution is intended to mean that the mixture is liquid and homogeneous and that it does not contain solid particles in suspension, all the solid elements of the mixture being entirely dissolved in one or more solvents which are miscible with one another.

Any solvent or mixture of solvents for the constituents of the composition can be envisaged for diluting the formulation, as long as it remains compatible with regulatory requirements linked to selling and using products used in the environment of animals and humans.

The solvents used to dilute the formulation are preferentially chosen from pure alcohols or alcohols mixed with water, aliphatic paraffins, glycol ethers, polyglycol ethers, or a mixture of at least two thereof.

When the solvent is an alcohol mixed with water, said mixture comprises an amount of water less than or equal to 30% by weight, preferably less than or equal to 20% by weight, even more preferentially less than or equal to 10% by weight. By way of example, the water/alcohol mixture is 30/70, 20/80 or else 10/90.

The aliphatic paraffins, the glycol ethers and the polyglycol ethers preferentially have a boiling point of between 200° C. and 330° C., preferably between 230° C. and 310° C.

In particular, the alcohols are chosen from alcohols consisting of 1 to 6 carbon atoms. Nonlimiting examples thereof are ethanol, isopropanol, methanol, butanol, isobutanol or pentanol. Ethanol and isopropanol are preferentially used.

The aliphatic paraffins are preferably chosen from the Isopar™ products sold by ExxonMobil Chemical Hydrocarbons.

The glycol ethers are preferentially chosen from glycol monomethyl, monopropyl or monobutyl ethers.

The polyglycol ethers are preferentially chosen from mono-, di-, tri- or polypropylene glycol methyl, ethyl, propyl or butyl ethers.

The nepetalactone present in the composition according to the invention is of synthetic origin or introduced in the form of plant extract: according to a particular embodiment of the invention, it derives from an extract of *Nepeta cataria*.

The composition according to the invention may also optionally comprise additional constituents such as, for example, antioxidants, stabilizers, drying promoters, dyes, fragrances. Such constituents must not, of course, have antagonistic effects on the attractant and soothing constituents of the composition. The composition according to the invention preferably does not contain cyclodextrin and/or irritant antibacterial agents such as chlorhexidine.

According to a particular embodiment, the soothing composition for non-human mammals consists of between 1% and 50% by weight/weight of at least one fatty acid comprising between 5 and 22 carbon atoms and between 0.01% and 5% by weight/weight of nepetalactone, and optionally additional constituents such as, for example, antioxidants, stabilizers, drying promoters, dyes, fragrances, characterized in that said fatty acid(s) and said nepetalactone are dissolved in a solvent; these ingredients and the preferred concentrations thereof being as defined above.

The composition according to the invention has the advantage of being stable and homogeneous in the form of a solution.

By stability over the duration of exposure or treatment, which is typically 30 days, the applicant means that the composition will retain at least 50% of its initial nepetalactone content (which corresponds to a half-life of the nepetalactone which is greater than or equal to the duration of treatment).

The compositions according to the present invention make it possible to prevent the stress felt by cats and to soothe cats, and consequently make it possible, inter alia, to avoid future marking, such as urine marking or scratching.

According to the invention, urine marking is intended to mean an odorizing stream of urine projected horizontally onto a vertical support by a non-human mammal. The odorizing stream of urine contains pheromones which especially have an alarm role for fellow creatures.

According to the invention, stress is intended to mean that the non-human mammal has an apprehension of danger and fear accompanied by conscious stress, which is reflected in a high probability of giving behavioral and emotional fear responses. In neurobiological terms, this stress state is accompanied by hyperactivity of the noradrenergic and serotonin systems.

The present invention also relates to a method for reducing signs of stress or anxiety in a non-human mammal, consisting in exposing the non-human mammal to a composition according to the invention; to a method for preventing and reducing urine marking and scratching in cats, consisting in exposing the cat to a composition according to the invention, and further to a method for facilitating the adaptation and the socialization of kittens, or for increasing their social interactions, consisting in exposing the kittens to a composition according to the invention.

The present invention also relates to a composition according to the invention for the use thereof in reducing manifestations of stress or anxiety in a non-human mammal, in particular felines, especially domestic cats.

It also relates to the use of a composition according to the invention for preventing and reducing urine marking and scratching in cats, and for facilitating the adaptation and the socialization of kittens, or for increasing their social interactions.

The composition according to the invention is preferentially brought into contact with the animal by diffusion into the area in which the animal is to develop, by means of a vaporizer or an electric diffuser or any other means known to those skilled in the art which enables the composition to diffuse into the environment of the non-human mammal.

Thus, the present invention relates to the use of a composition according to the invention in electric diffusers or vaporizers, for diffusing a soothing composition, and to the use of a composition according to the invention in electric diffusers or vaporizers, for diffusing a composition for preventing marking, such as urine marking and scratching.

According to the invention, diffusion is intended to mean the propagation of the product by release, whether via vaporization or by means of an electric diffuser.

According to the invention, "attractant effect" is intended to mean that cats, or non-human mammals, are attracted by the odor of this compound.

The process for manufacturing the composition according to the invention preferably consists in dissolving the fatty acid(s) in the solvent under hot conditions, then, when the mixture is homogeneous, introducing nepetalactone of synthetic origin or in the form of a plant extract into said mixture at room temperature, until a homogeneous composition is obtained. This manufacturing process is preferentially carried out with constant stirring in a closed reactor. The fatty acid mixing under hot conditions is preferentially carried out at between 40° C. to 80° C. Even more preferentially, this mixing may be carried out at 45° C.

FIGURES

EXAMPLES

Figure 1:
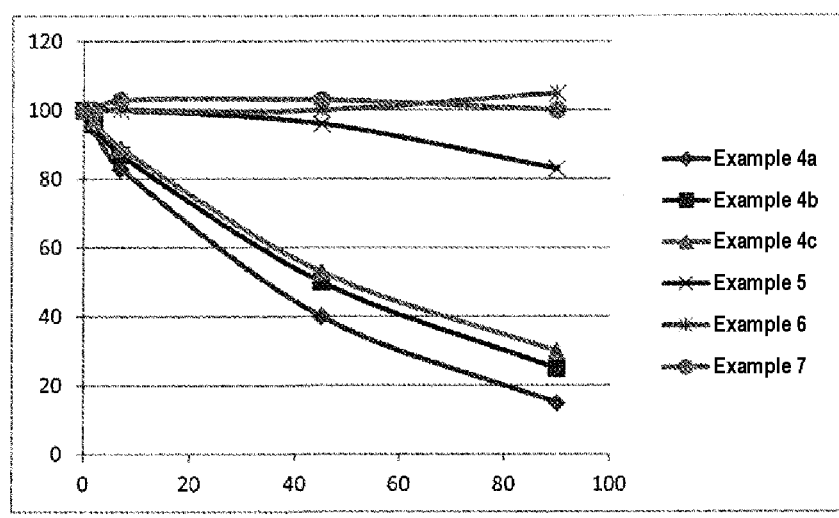
FIG. 1 is a graph comprising curves illustrating the degradation over time (in days) of nepetalactone at 40° C. for examples 4 to 7.

The stability of nepetalactone is monitored by gas chromatography (GC). The samples are kept in a ventilated oven at 40° C. and aliquots are analyzed regularly. The product is considered to be sufficiently stable when the half-life of the nepetalactone in the mixture at 40° C. is greater than 20 days (which equates to 30 days at 25° C.).

The results are expressed as weight percentage of nepetalactone relative to the initial amount. The analyses were carried out under the following conditions: Hewlett Packard GC apparatus (5890 Series II), fitted with a FID detector (Flame Ionization Detector) and an HP5 column (Agilent J&W) 30 m×0.53 mm, film 0.88 µm, with a helium pressure of 11 psi, an injector temperature of 250° C. and a detector temperature of 280° C. The following were also used: an initial oven temperature of 100° C., an initial time of 3 min; a ramp 1 of 30° C./min, a final temperature 1 of 170° C. and a stage time 1 of 3 min; a ramp 2 of 5° C./min, a final temperature 2 of 250° C.; a ramp 3 of 20° C./min, a final temperature of 280° C. and a final stage time of 4 min.

The samples to be analyzed were prepared by diluting 600 mg of stabilized sample in ethanol (QSP 20 ml). The volume of sample injected into the GC is 1 µl.

The nepetalactone used for illustrating the invention is obtained commercially from Berjé in the form of an extract of *Nepeta cataria* which contains approximately 80% nepetalactone.

Example 1: Analysis of the Stability of 0.8% Nepetalactone in Linoleic Acid 100 mg of extract of *Nepeta cataria* is added to 9.9 g of linoleic acid. This solution is placed in an oven at 40° C. Aliquots are taken at 14.5 h, 24 h and 45 h.

The analysis of the stability at 40° C. of a 0.8% solution of nepetalactone in linoleic acid is presented in table I below.

TABLE I stability at 40° C. of a 0.8% by weight
solution of nepetalactone in linoleic acid

| Time (days) | % degradation of nepetalactone |
|---|---|
| 0 | — |
| 0.5 | 4.4% |
| 1 | 15% |
| 2 | 19.5% |

This example shows that, at a content of 0.8% by weight in linoleic acid, after only 1 day, the composition lost 15% of its nepetalactone content, which makes such a composition unusable since the effect of the nepetalactone would decrease too quickly over the duration of use of the composition as soothing agent for non-human mammals. The half-life of this composition is estimated at only 12 days.

Example 2: Analysis of the Stability of Nepetalactone in a 85/15 Linoleic Acid/Extract of *Nepeta cataria* Mixture 1.5 g of extract of *Nepeta cataria* are added to 8.5 g of linoleic acid. This solution is placed in an oven at 40° C. Aliquots are taken regularly for analysis.

The analysis of the stability at 40° C. of a solution at 12% by weight, relative to the total weight of the solution, of nepetalactone in linoleic acid is presented in table II below.

TABLE II stability at 40° C. of a 12% solution
of nepetalactone in linoleic acid

| Time (days) | % degradation of nepetalactone |
|---|---|
| 0 | — |
| 0.5 | 4.4% |
| 1 | 7.5% |
| 2 | 11.7% |

Approximately 12% of nepetalactone is degraded after 2 days. This gives a half-life of 13 days, which makes this mixture unsuitable for the desired application. Moreover, the slower kinetics than in example 1 suggests that the degradation of the nepetalactone is governed by the fatty acid content.

Example 3: Analysis of the Stability of Nepetalactone in the Presence of a Synthetic F3 Fraction of Cat Facial Pheromone a) Synthetic Replica of an F3 Fraction of Cat Facial Pheromone The replica F3 fraction of cat facial pheromones corresponds to that used in the product sold by CEVA under the brand name Feliway®. More specifically, the authors used GCMS to analyze products sold under the brand name Feliway® containing the synthetic F3 fraction.

The composition identified in the samples and reproduced for the tests is as follows:

| Compound | Composition of the F3 fraction according to analysis of the commercial product Feliway® (g) | Amount of components used to manufacture 100 g of replica F3 fraction of cat facial pheromone (g) |
|---|---|---|
| Pimelic acid | 3.04 | 3.05 |
| Ethyl pimelate | 2.88 | 2.89 |
| Diethylpimelate | 0.42 | 0.42 |
| Azelaic acid | 3.4 | 3.4 |
| Monomethylnonanedioate | 2.7 | 2.7 |
| Decanoic acid | 0.15 | 0.16 |
| Ethyl decanoate | 0.12 | 0.12 |
| Lauric acid | 2.9 | 2.89 |
| Ethyl laurate | 0.8 | 0.81 |
| Palmitic acid | 10.85 | 10.86 |
| Ethyl palmitate | 4.6 | 4.59 |
| Cis-13-octadecenoic acid | 40 | 40 |
| Ethyl oleate | 27 | 27 |

Formulation is carried out at 45° C., starting by introducing the oleic derivatives so as to entirely dissolve all the components. Stability of nepetalactone in the F3 fraction b) Stability of Nepetalactone in the F3 Fraction 100 mg of nepetalactone in the form of extracts of *Nepeta cataria* are added to 9.9 g of the F3 fraction thus obtained at 70% in ethanol. This solution is placed in an oven at 40° C. Aliquots are taken at different time intervals. The analysis of the stability at 40° C. of a 70% solution of F3 fraction, containing 0.8% by weight, relative to the total weight of the solution, of nepetalactone, is presented in table III below.

TABLE III stability at 40° C. of a 0.8% by weight
solution of nepetalactone in an F3
fraction obtained at 70% in ethanol

| Time (days) | % degradation of nepetalactone |
|---|---|
| 0 | — |
| 1 | 7.4% |
| 2 | 19.7% |

A similar degradation is observed to that observed in example 1; again, it makes such a composition unusable since the nepetalactone content decreases too quickly. The faster kinetics than in test 2 show that the F3 fraction degrades the nepetalactone more quickly than linoleic acid.

Example 4a-c: Preparation of Alcoholic Solutions of Linoleic Acid and Extract of *Nepeta cataria* in a 95/5 Ratio General procedure: 9.5 g of linoleic acid are dissolved in a volume of isopropanol at 40° C., then after returning to room temperature 0.5 g of nepetalactone in the form of extract of *Nepeta cataria* is added.

The solutions prepared are characterized by the volume of isopropanol used and summarized in the following table IV.

TABLE IV alcoholic solutions 4a, 4b and 4c of linoleic acid and extract of *Nepeta cataria* in a 95/5 ratio

|  | Linoleic acid (g) (%) | Extract of *Nepeta cataria* (g) (% nepetalactone) | Isopropanol (g) (%) |
|---|---|---|---|
| Example 4a | 9.5 (47.5%) | 0.5 (2%) | 10 (50%) |
| Example 4b | 9.5 (31.7%) | 0.5 (1.36%) | 20 (66%) |
| Example 4c | 9.5 (19%) | 0.5 (0.8%) | 40 (80%) |

Example 5: Preparation of Alcoholic Solutions of F3 Fraction and Nepetalactone According to the Invention The procedure as in example 3 is carried out, mixing 10 g of F3 fraction with 90 g of denatured water-ethanol (10/90) mixture, then 0.5 g of extract of *Nepeta cataria* is added. These mixing operations are carried out at room temperature, and the final mixture is homogeneous. The initial content of nepetalactone measured (relative to the chromatographic area and in comparison with a pure nepetalactone standard) is 0.4% by weight relative to the total weight of the solution.

Example 6: Preparation of Paraffinic Solutions of F3 Fraction and Nepetalactone

The F3 fraction is prepared as in example 3, mixing 2 g of F3 fraction in 97.5 g of paraffin at 45° C. The mixture is left to return to room temperature, then 0.5 g of nepetalactone is added. After brief stirring, a translucent mixture is obtained. The nepetalactone in the mixture is assayed relative to an external standard.

Example 7: Preparation of Polyglycolic Solutions of F3 Fraction and Nepetalactone The F3 fraction is prepared as in example 5, mixing 2 g of F3 fraction in 97.5 g of dipropylene glycol propyl ether at 35° C. The mixture is left to return to room temperature, then 0.5 g of nepetalactone is added. After brief stirring, a translucent mixture is obtained.

Example 8: Analysis of the Stability of the Compositions of Examples 4 to 7

All the samples are packaged in climatic chambers at 40° C. and 75% moisture, upside-down for the sprays (in order to guarantee the leaktightness of the bottles and avoid side reactions which could lead to the presence of air).

The results of the analysis of stability are presented in table V below.

TABLE V

Change in the content of nepetalactone over time relative to initial content (in % remaining)
(values greater than 100 are due to measurement precision; values in italics are extrapolated over a trend curve with a correlation coefficient of greater than 99%)

| number of days | 0 | 1 | 2 | 7 | 45 | 90 |
|---|---|---|---|---|---|---|
| Example 4a | 100 | 98 | 95 | 83 | *40* | *15* |
| Example 4b | 100 | 100 | 96 | 87 | *50* | *25* |
| Example 4c | 100 | 100 | 97 | 89 | *53* | *30* |
| Example 5 | 100 | 100 | 100 | 100 | 96 | 83 |
| Example 6 | 100 | 100 | 100 | 100 | 100 | 105 |
| Example 7 | 100 | 100 | 100 | 103 | 103 | 100 |

All these examples have a half-life of the nepetalactone in the mixture, at 40° C., of greater than 20 days. As expected, it can be seen that the degradation kinetics slow down as a function of the reduction in concentration. The change in kinetics as a function of concentration indicates that the limit of composition which makes it possible to have a half-life at 40° C. of greater than 20 days is approximately 45% isopropanol, 50% linoleic acid and 5% extract of nepetalactone.

Example 9: Study of Effectiveness of the Compositions According to the Invention The study is carried out with a group of 24 healthy adult cats, at least 12 months old at the start of the study, divided into four groups. Arterial pressure was never measured on any of the cats: this act of handling is the event which causes the stress in the animal, in this example.

Two products were tested:
  the composition resulting from the present invention, prepared according to example 5 in a 20 ml vaporizer;
  the commercial product Feliway® in a 20 ml vaporizer (Ceva, France), which contains a synthetic analog of the F3 fraction (10%), and ethanol q.s.p. 20 ml, and which represents the positive control which makes it possible to standardize the results obtained with the composition prepared according to example 5.

The study comprises a period of administration of 5 days and a period of withdrawal of at least 9 days. 2 groups of 6 cats received the product tested first, and the 2 others received the positive control. All the cats then changed, taking the other product, such that each product was tested by the 24 cats.

The arterial pressure of each cat was measured at the start and at the end of the period of exposure to the composition. The latter was sprayed for three consecutive days following the day on which the first measurement of arterial pressure was taken and the day on which the second measurement of arterial pressure was taken. All the products were sprayed in 5 applications (volume of product of 0.15 ml per application) in each corner of each study room 3 times daily.

Acceptance of the arterial pressure measurement and of the overall procedure was evaluated by taking into account different somatic attitudes (which are characteristic of aggressive, wary and soothed behaviors) and the intensity of these behaviors. This evaluation enables a behavioral well-being score to be obtained, which is reflected in a low score when the cat is sensitive to stress, and a high score when the cat is soothed.

These behavioral observations were carried out at different times:
  30-40 minutes before handling, during handling, 30 to 40 minutes after handling, and 4-5 hours after handling.

In order to evaluate the impact of the novel composition, the mean of the scores for stress obtained with each product (product tested and Feliway® positive control) was calculated at the different times mentioned above, during day 1 and again at day 5.

The difference in the scores between day 1 (before exposure to the composition) and 5 (at the end of the period of exposure) was then compared for the composition prepared according to example 5, standardized using the positive control at the evaluation points in order to identify the impact of the novel composition.

Figure 2:
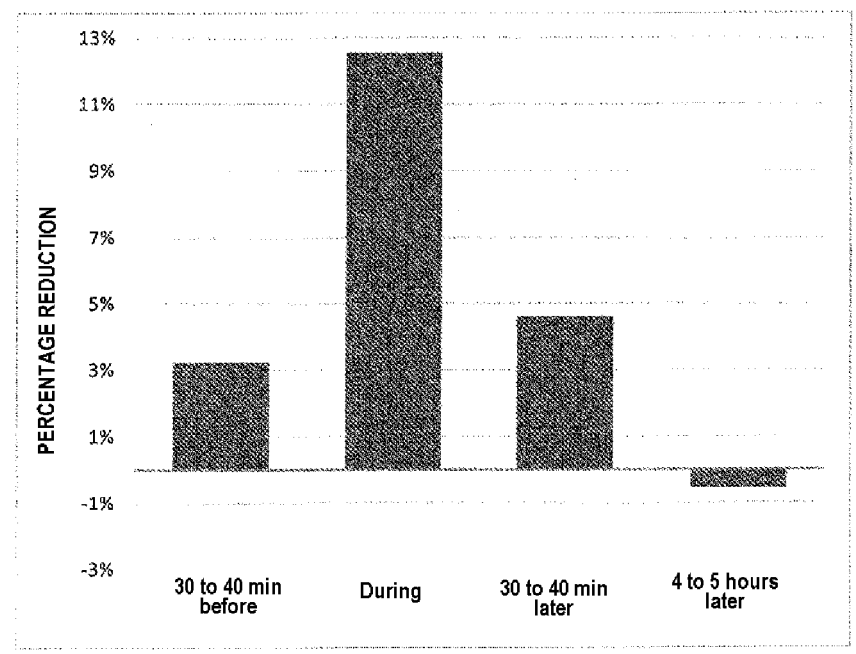
FIG. 2 is a histogram representing the percentage reduction in behavioral scores evaluated during an episode of stress in cats exposed to the composition prepared according to example 5, standardized to the positive control as described in example 9.

The study results showed a difference between the positive control and the product tested according to the invention at different times (FIG. 2). During the central stressing event (measurement of arterial pressure), the product tested according to the invention provided a statistically significant reduction in the stress index compared to the positive control. 4 to 5 hours after the measurement of arterial pressure, a very small numerical difference was noted, without statistical significance.

The combination of the synthetic analog of the F3 fraction and nepetalactone enables better management of stress in domestic cats than with the F3 fraction alone (Feliway®). Such a combination may be a novel tool for managing moderate behavioral disorders, especially in the case of immediate or acute stress. This composition may also be used for facilitating the adaptation and the socialization of non-human mammals, in particular kittens, and for increasing social interactions and playful behavior.

The invention claimed is:

1. A soothing composition for non-human mammals, comprising fatty acid(s) comprising between 5 and 22 carbon atoms, and nepetalactone,
    wherein the whole content of the fatty acid(s) comprising between 5 and 22 carbon atoms in the composition is between 1% and 20% by weight/weight and the content of the nepetalactone is between 0.01% and 5% by weight/weight,
    wherein the fatty acid(s) and the nepetalactone are dissolved in a solvent, and
    wherein the composition does not contain any other fatty acid.

2. The composition as claimed in claim 1, wherein the non-human mammal is a feline.

3. The composition as claimed in claim 2, wherein the feline is a domestic cat.

4. The composition as claimed in claim 1, wherein the fatty acid(s) are selected from the group consisting of oleic, linoleic, linolenic, palmitic, myristic, azelaic, pimelic, capric, lauric acid, and a mixture of at least two thereof.

5. The composition as claimed in claim 1, wherein the fatty acid(s) are among the fatty acids which constitute the F3 fraction of the cat facial pheromones.

6. The composition as claimed in claim 1, wherein the solvent is selected from the group consisting of pure alcohols, alcohols mixed with water, aliphatic paraffins, glycol ethers, polyglycol ethers, and a mixture of at least two thereof.

7. The composition as claimed in claim 6, wherein the aliphatic paraffins, the glycol ethers and the polyglycol ethers have a boiling point of between 200° C. and 330° C.

8. The composition as claimed in claim 6, wherein the polyglycol ethers are selected from the group consisting of mono-, di-, tri- and polypropylene glycol methyl, ethyl, propyl or butyl ethers.

9. The composition as claimed in claim 6, wherein the aliphatic paraffins, the glycol ethers and the polyglycol ethers have a boiling point of between 230° C. and 310° C.

10. The composition as claimed in claim 1, where the nepetalactone used is of synthetic origin or introduced in the form of a plant extract.

11. The composition as claimed in claim 10, wherein the nepetalactone used is derived from an extract of *Nepeta cataria*.

12. The composition as claimed in claim 1, wherein the content of fatty acid(s) is between 1% and 15% by weight/weight.

* * * * *